United States Patent [19]

Chou

[11] Patent Number: 4,659,724

[45] Date of Patent: Apr. 21, 1987

[54] CERTAIN 1-[4-(5-CYANO-2-PYRIDYLOXY)PHENYL-BENZOYL UREAS HAVING PESTICIDAL PROPERTIES

[75] Inventor: David T. Chou, Raleigh, N.C.

[73] Assignee: Union Carbide Corporation, Danbury, Conn.

[21] Appl. No.: 727,678

[22] Filed: Apr. 26, 1985

Related U.S. Application Data

[63] Continuation of Ser. No. 454,847, Dec. 30, 1982, abandoned.

[51] Int. Cl.$^4$ .................... C07D 213/64; A01N 43/40
[52] U.S. Cl. .................................. 514/344; 546/288; 546/296; 546/297; 546/300; 546/302
[58] Field of Search ............... 546/288, 296, 297, 300, 546/302; 514/344

[56] References Cited

U.S. PATENT DOCUMENTS

| | | | |
|---|---|---|---|
| 3,992,553 | 11/1976 | Sirrenberg et al. | 514/522 |
| 4,005,223 | 1/1977 | Sirrenberg et al. | 514/594 |
| 4,026,937 | 5/1977 | Gulbenk | 260/293.69 |
| 4,041,177 | 8/1977 | Sirrenberg et al. | 514/597 |
| 4,064,267 | 12/1977 | Sirrenberg et al. | 514/522 |
| 4,173,637 | 11/1979 | Nishiyama et al. | 514/351 |
| 4,173,638 | 11/1979 | Nishiyama et al. | 514/351 |
| 4,194,005 | 3/1980 | Sirrenberg et al. | 514/522 |
| 4,310,530 | 1/1982 | Nishiyama et al. | 514/351 |
| 4,321,388 | 3/1982 | Nishiyama et al. | 546/291 |

FOREIGN PATENT DOCUMENTS

| | | | |
|---|---|---|---|
| 0025363 | 3/1981 | European Pat. Off. | 564/44 |
| 5038356 | 9/1978 | Japan | 564/44 |
| 5038357 | 9/1978 | Japan | 564/44 |
| 5079369 | 12/1978 | Japan | 546/291 |
| 6015272 | 7/1979 | Japan | 546/291 |
| 6025144 | 8/1979 | Japan | 546/291 |
| 7002258 | 5/1980 | Japan | 546/291 |
| 8039657 | 9/1981 | Japan | 546/291 |
| 2058072 | 4/1981 | United Kingdom | 546/291 |
| 2083360 | 3/1982 | United Kingdom | 564/44 |

*Primary Examiner*—Alan L. Rotman
*Attorney, Agent, or Firm*—Gerald L. Coon

[57] ABSTRACT

Novel pyridyloxyaryl benzoyl ureas and a process for their preparation are provided. The novel ureas are useful as the active toxicant in insecticidal compositions.

26 Claims, No Drawings

CERTAIN 1-[4-(5-CYANO-2-PYRIDYLOXY)PHENYL-BENZOYL UREAS HAVING PESTICIDAL PROPERTIES

FIELD OF INVENTION

This application is a continuation of prior U.S. application Ser. No. 454,847, filed Dec. 30, 1982, now abandoned.

This invention relates in general to novel pyridyloxaryl benzoyl ureas, pesticidal compositions containing the ureas and a process for their preparation. In one aspect, this invention relates to benzoyl ureas which are useful as pesticides.

BACKGROUND OF THE INVENTION

Prior to the present invention several benzoyl ureas had been reported in the patent literature as having pesticidal activity. For example, U.S. Pat. No. 4,173,637 which issued Nov. 6, 1979 disclosed certain N-benzoyl-N'-pyridyloxy phenyl ureas having a halogen, nitro or trifluoromethyl group as a substituent in the five-positron of the pyridyl group. U.S. Pat. No. 4,194,005 also discloses certain cyano-substituted phenoxy phenyl benzoyl ureas. U.S. Pat. No. 4,310,530 which issued on Jan. 12, 1982 discloses trifluoromethyl-substituted pyridyloxy phenyl benzoyl urea. Other trifluromethyl-substituted pyridyl ureas are disclosed and claimed in U.S. Pat. No. 4,321,388 which is assigned to Ishihara Sangyo Kaisha Ltd. of Japan. Additional disclosures of benzoyl ureas in the patent literature are found in British Pat. No. 2083360, European Pat. No. 40,179 as well as in U.S. Pat. Nos. 4,344,951; 3,992,553; 4,005,223; 4,041,177; and 4,064,267. Thus, prior to the present invention relatively few materials of this class have been claimed useful as pesticides.

Accordingly, one or more of the following objects can be achieved by the practice of this invention. It is an object of this invention to provide novel pyridyloxyaryl benzoyl ureas. Another object of this invention is to provide certain 1-(pyridyloxyphenyl)-3-benzoyl ureas which exhibit excellent insecticidal activity. A further object is to provide processes for the preparation of the novel benzoyl ureas. A still further object is to provide novel pesticidal compositions containing the novel benzoyl ureas as the active toxicant. Another object of the invention is to provide a method for controlling pests by the application of the novel pesticidal compositions. These and other objects will readily become apparent to those skilled in the art in the light of the teachings herein set forth.

SUMMARY OF THE INVENTION

In its broad aspect the invention relates to novel 1-(pyridyloxyaryl)-3-benzoyl ureas, pesticidal compositions containing the same, and processes for their preparation and use. The benzoyl ureas of this invention can be represented by the following formula 1:

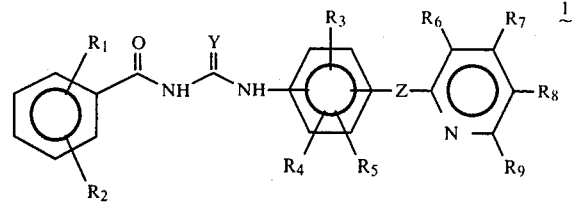

wherein: $R_1$, $R_2$, $R_3$, $R_4$, $R_5$, $R_6$, $R_7$, $R_8$, $R_9$, Y and Z are as hereinafter described.

DETAILED DESCRIPTION OF THE INVENTION

As indicated above, this invention is directed to novel benzoyl ureas which can be represented by the following formula:

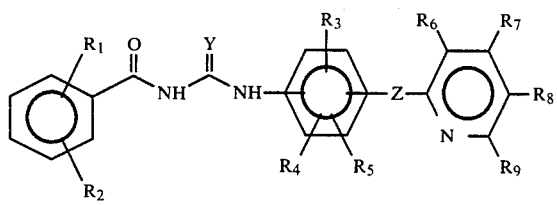

Wherein:
Y represents oxygen or sulfur.
Z represents oxygen, sulfur, sulfinyl or sulfonyl;
$R_1$, $R_2$ are independently hydrogen, halogen, methyl, trifluoromethyl, lower alkyl;
$R_3$, $R_4$, $R_5$ are independently hydrogen, halogen, trifluoromethyl, methyl;
$R_6$ represents hydrogen, halogen, lower alkyl, cyano, nitro;
$R_7$ may be hydrogen, halogen, lower alkyl;
$R_8$ may be lower alkyl, cyano, nitro, hydrogen and halogen;
$R_9$ is hydrogen, halogen, or lower alkyl, provided that when $R_7$ and $R_9$ are hydrogen and $R_6$ is hydrogen, halogen or nitro, $R_8$ may not be hydrogen, halogen or nitro. A preferred class of benzoyl ureas within the above generic formula are of the formula:

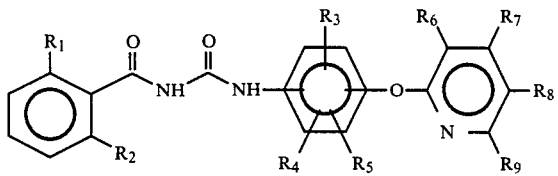

wherein:
$R_1$, $R_2$ are independently hydrogen, halogen, methyl, trifluoromethyl, or lower alkyl;
$R_3$, $R_4$, and $R_5$ are independently hydrogen, halogen, trifluoromethyl, or methyl;
$R_6$ represents hydrogen, halogen, lower alkyl, cyano, or nitro;
$R_7$ represents hydrogen, halogen, or lower alkyl;
$R_8$ represents lower alkyl, cyano, nitro, hydrogen or halogen; and
$R_9$ is hydrogen, halogen, or lower alkyl, provided that when $R_7$ and $R_9$ are hydrogen and $R_6$ is hydrogen, halogen or nitro, $R_8$ may not be hydrogen, halogen or nitro.

Another class of benzoyl ureas within the aforementioned generic formula are the thioureas of the formula

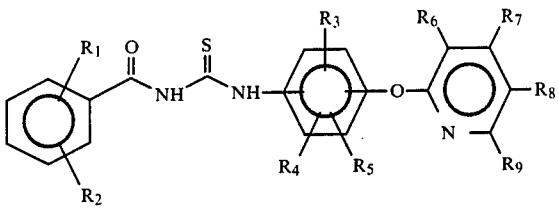

wherein:
$R_1$, $R_2$ are independently hydrogen, halogen, methyl, trifluoromethyl, or lower alkyl;
$R_3$, $R_4$, or $R_5$ are independently hydrogen, halogen, trifluoromethyl, or methyl;
$R_6$ represents hydrogen, halogen, lower alkyl, cyano, or nitro;
$R_7$ represents hydrogen, halogen, or lower alkyl;
$R_8$ represents lower alkyl, cyano, nitro, hydrogen or halogen; and
$R_9$ is hydrogen, halogen, or lower alkyl, provided that when $R_7$ and $R_9$ are hydrogen and $R_6$ is hydrogen, halogen or nitro, $R_8$ may not be hydrogen, halogen or nitro.

A further class of benzoyl ureas encompassed by the generic formula are the pyridylthio phenyl ureas of the formula:

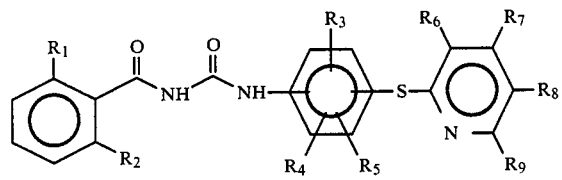

wherein:
$R_1$, $R_2$ are independently hydrogen, halogen, methyl, trifluoromethyl, or lower alkyl;
$R_3$, $R_4$, or $R_5$ are independently hydrogen, halogen, trifluoromethyl, or methyl;
$R_6$ represents hydrogen, halogen, lower alkyl, cyano, or nitro;
$R_7$ represents hydrogen, halogen, or lower alkyl;
$R_8$ represents lower alkyl, cyano, nitro, hydrogen or halogen; and
$R_9$ is hydrogen, halogen, or lower alkyl, provided that when $R_7$ and $R_9$ are hydrogen and $R_6$ is hydrogen or halogen, $R_8$ may not be hydrogen, halogen or nitro.

The novel benzoyl urea compounds disclosed herein are illustrated by, but not limited to, the following:
1-[4-(3-chloro-5-cyano-2-pyridyloxy)-3,5-dibromophenyl]-3-(2,6-difluorobenzoyl)urea,
1-[4-(3-chloro-5-cyano-2-pyridyloxy)-3,5-dibromophenyl]-3-(2-chlorobenzoyl)urea,
1-[4-(3-chloro-5-cyano-2-pyridyloxy)-3,5-dibromophenyl]-3-(2-chloro-6-fluorobenzoyl urea,
1-[4-(3-cyano-2-pyridyloxy)-3,5-dibromophenyl]-3-(2,6-difluorobenzoyl)urea,
1-[4-(5-cyano-2-pyridyloxy)-3,5-dibromophenyl]-3-(2-chlorobenzoyl)urea,
1-[4-(5-cyano-2-pyridyloxy)-3,5-dibromophenyl]-3-(2-chloro-6-fluorobenzoyl)urea,
1-[4-(5-cyano-2-pyridyloxy)-3,5-dibromophenyl]-3-(2,6-dichlorobenzoyl)urea,
1-[4-(5-cyano-2-pyridyloxy)-3,5-dimethylphenyl]-3-(2,6-difluorobenzoyl)urea,
1-[4-(5-cyano-2-pyridyloxy)-3,5-dimethylphenyl]-3-(2-chlorobenzoyl)urea,
1-[4-(5-cyano-2-pyridyloxy)-3,5-dimethylphenyl]-3-(2,6-dichlorobenzoyl)urea,
1-[4-(5-cyano-2-pyridyloxy)-3,5-dimethylphenyl]-3-(2-fluorobenzyl)urea,
1-[4-(3-chloro-5-cyano-2-pyridyloxy)-3,5-dimethylphenyl]-3-(2-6-difluorobenzoyl)urea,
1-[4-(3-chloro-5-cyano-2-pyridyloxy)-3,5-dimethylphenyl]-3-(2-6-dichlorobenzoyl)urea,
1-[4-(3-chloro-5-cyano-2-pyridyloxy)-3,5-dimethylphenyl]-3-(2-chloro-6-fluorobenzoyl)urea,
1-[4-(5-cyano-2-pyridyloxy)-3-trifluoromethylphenyl]-3-(2-chlorobenzoyl)urea,
1-[4-(5-cyano-2-pyridyloxy)-3-trifluoromethylphenyl]-3-(2,6-difluorobenzoyl)urea,
1-[4-(5-cyano-2-pyridyloxy)-3-trifluoromethylphenyl]-3-(2,6-difluorobenzoyl)urea,
1-[4-(5-cyano-2-pyridyloxy)-3-trifluoromethylphenyl]-3-(2,6-dichlorobenzoyl)urea,
1-[4-(3-chloro-5-cyano-2-pyridyloxy)-3-trifluoromethylphenyl]-3-(2-chlorobenzoyl)urea,
1-[4-(3-chloro-5-cyano-2-pyridyloxy)-3-trifluoromethylphenyl]-3-(2,6-difluorobenzoyl)urea,
1-[4-(3-chloro-5-cyano-2-pyridyloxy)-3-trifluoromethylphenyl]-3-(2,6-dichlorobenzoyl)urea,
1-[4-(3-chloro-5-cyano-2-pyridyloxy)-3-trifluoromethylphenyl]-3-(2-chloro-6-fluorobenzoyl)urea,
1-[4-(3-chloro-5-cyano-2-pyridyloxy)-3,6-dimethyl-5-chlorophenyl]-3-(2-chlorobenzoyl)urea,
1-[4-(3-chloro-5-cyano-2-pyridyloxy)-3,6-dimethyl-5-chlorophenyl]-3-(2,6-difluorobenzoyl)urea,
1-[4-(3-chloro-5-cyano-2-pyridyloxy)-3,6-dimethyl-5-chlorophenyl]-3-(2,6-dichlorobenzoyl)urea,
1-[4-(3-chloro-5-cyano-2-pyridyloxy)-3,6-dimethyl-5-chlorophenyl]-3-(2-chloro-6-fluorobenzoyl)urea,
1-[4-(3-methyl-5-nitro-2-pyridyloxy)-3,5-dibromophenyl]-3-(2-chlorobenzoyl)urea,
1-[4-(3-methyl-5-nitro-2-pyridyloxy)-3,5-dibromophenyl]-3-(2,6-difluorobenzoyl)urea,
1-[4-(3-methyl-5-nitro-2-pyridyloxy)-3,5-dibromophenyl]-3-(2,6-dichlorobenzoyl)urea,
1-[4-(3-methyl-5-nitro-2-pyridyloxy)-3,5-dibromophenyl]-3-(2-chloro-6-fluorobenzoyl)urea,
1-[4-(3-methyl-5-nitro-2-pyridyloxy)-3,6-dimethyl-5-chlorophenyl]-3-(2-chlorobenzoyl)urea,
1-[4-(3-methyl-5-nitro-2-pyridyloxy)-3,6-dimethyl-5-chlorophenyl]-3-(2,6-difluorobenzoyl)urea,
1-[4-(3-methyl-5-nitro-2-pyridyloxy)-3,6-dimethyl-5-chlorophenyl]-3-(2,6-dichlorobenzoyl)urea,
1-[4-(3-methyl-5-nitro-2-pyridyloxy)-3,6-dimethyl-5-chlorophenyl]-3-(2-chloro-6-fluorobenzoyl)urea,
1-[4-(5-cyano-2-pyridyloxy)-3,6-dimethyl-5-chlorophenyl]-3-(2-chlorobenzoyl)urea,
1-[4-(5-cyano-2-pyridyloxy)-3,6-dimethyl-5-chlorophenyl]-3-(2-chlorobenzoyl)urea,
1-[4-(5-cyano-2-pyridyloxy)-3,6-dimethyl-5-chlorophenyl]-3-(2,6-dichlorobenzoyl)urea,
1-[4-(5-cyano-2-pyridyloxy)-3,6-dimethyl-5-chlorophenyl]-3-(2,6-difluorobenzoyl)urea,
1-[4-(5-cyano-2-pyridyloxy)-3,6-dimethyl-5-chlorophenyl]-3-(2-chloro-6-fluorobenzoyl)urea, 1-[4-(3-methyl-5-cyano-2-pyridyloxy)-3-methylphenyl]-3-(2-chlorobenzoyl)urea,
1-[4-(3-methyl-5-cyano-2-pyridyloxy)-3-methylphenyl]-3-(2,6-difluorobenzoyl)urea,
1-[4-(3-methyl-5-cyano-2-pyridyloxy)-3-methylphenyl]-3-(2,6-dichlorobenzoyl)urea,
1-[4-(3-methyl-5-cyano-2-pyridyloxy)-3-methylphenyl]-3-(2-chloro-6-fluorobenzoyl)urea,
1-[4-(3-chloro-5-cyano-2-pyridyloxy)-3-methylphenyl]-3-(2-chlorobenzoyl)urea,
1-[4-(3-chloro-5-cyano-2-pyridyloxy)-3-methylphenyl]-3-(2,6-difluorobenzoyl)urea,
1-[4-(3-chloro-5-cyano-2-pyridyloxy)-3-methylphenyl]-3-(2,6-dichlorobenzoyl)urea,
1-[4-(3-chloro-5-cyano-2-pyridyloxy)-3-methylphenyl]-3-(2-chloro-6-fluorobenzoyl)urea,
1-[4-(3-chloro-5-cyano-2-pyridyloxy)-3-methylphenyl]-3-(2-methylbenzoyl)urea,
1-[4-(3-chloro-5-cyano-2-pyridyloxy)-3-methylphenyl]-3-(2-trifluoromethylbenzoyl)urea,
1-[4-(3-chloro-5-cyano-2-pyridylthio)phenyl]-3-(2-chlorobenzoyl)urea,
1-[4-(3-chloro-5-cyano-2-pyridylthio)phenyl]-3-(2,6-difluorobenzoyl)urea,
1-[4-(3-chloro-5-cyano-2-pyridylthio)phenyl]-3-(2,6-dichlorobenzoyl)urea,
1-[4-(3-chloro-5-cyano-2-pyridylthio)phenyl]-3-(2-chloro-6-fluorobenzoyl)urea,
1-[4-(3-chloro-5-cyano-2-pyridyloxy)-3,5-dimethylphenyl]-3-(2,6-difluorobenzoyl)thiourea,
1-[4-(3-chloro-5-cyano-2-pyridyloxy)-3,5-dibromophenyl]-3-(2,6-difluorobenzoyl)thiourea,
1-[4-(5-cyano-2-pyridyloxy)-3,5-dibromophenyl]-3-(2,6-difluorobenzoyl)thiourea,
1-[4-(5-cyano-2-pyridyloxy)-3,6-dimethyl-5-chlorophenyl]-3-(2,6-difluorobenzoyl)thiourea,
1-[4-(5-cyano-2-pyridyloxy)-3,6-dimethyl-5-chlorophenyl]-3-(4-chlorobenzoyl)urea,
1-[4-(5-cyano-2-pyridyloxy)-3,6-dimethyl-5-chlorophenyl]-3-(4-chlorobenzoyl)thiourea,
1-[4-(5-cyano-2-pyridyloxy)-3,5-dibromophenyl]-3-(4-chlorobenzoyl)thiourea,
1-[4-(3-methyl-5-nitro-2-pyridyloxy)-3,5-dibromophenyl]-3-(2,6-difluorobenzoyl)thiourea,
1-[4-(3-methyl-5-nitro-pyridyloxy)-3,5-dibromophenyl]-3-(4-chlorobenzoyl)thiourea,
1-[4-(3-cyano-5-methyl-2-pyridyloxy)-3,5-dichlorophenyl]-3-(2-chlorobenzoyl)urea,
1-[4-(3-cyano-5-methyl-2-pyridyloxy)-3,5-dichlorophenyl]-3-(2,6-difluorobenzoyl)urea,
1-[4-(3-cyano-5-methyl-2-pyridyloxy)-3,5-dichlorophenyl]-3-(2,6-dichlorobenzoyl)urea,
1-[4-(3-cyano-5-methyl-2-pyridyloxy)-3,5-dichlorophenyl]-3-(2-chloro-6-fluorobenzoyl)urea,
1-[4-(3-cyano-5-methyl-2-pyridyloxy)-3,5-dichlorophenyl]-3-(2,6-difluorobenzoyl)thiourea,
1-[4-(3-cyano-5-methyl-2-pyridyloxy)-3,5-dichlorophenyl]-3-(4-chlorobenzoyl)thiourea,
1-[4-(3-cyano-5-methyl-2-pyridyloxy)-3,5-dichlorophenyl]-3-(2,6-dimethylbenzoyl)urea,
1-[4-(3-cyano-4,6-dimethyl-2-pyridyloxy)-3,5-dichlorophenyl]-3-(2,6-difluorobenzoyl)urea,
1-[4-(3-cyano-4,6-dimethyl-2-pyridyloxy)-3,5-dichlorophenyl]-3-(2,6-dichlorobenzoyl)urea,
1-[4-(3-cyano-4,6-dimethyl-2-pyridyloxy)-3,5-dichlorophenyl]-3-(2-chlorobenzoyl)urea,
1-[4-(3-cyano-4,6-dimethyl-2-pyridyloxy)-3,5-dichlorophenyl]-3-(2-chloro-6-fluorobenzoyl)urea,
1-[4-(3-cyano-4,6-dimethyl-2-pyridyloxy)-3,5-dichlorophenyl]-3-(2,6-difluorobenzoyl)thiourea,
1-[4-(5-cyano-6-chloro-2-pyridyloxy)-3,5-dichlorophenyl]-3-(2-chlorobenzoyl)urea,
1-[4-(5-cyano-6-chloro-2-pyridyloxy)-3,5-dichlorophenyl]-3-(2,6-difluorobenzoyl)urea,
1-[4-(5-cyano-6-chloro-2-pyridyloxy)-3,5-dichlorophenyl]-3-(2,6-dichlorobenzoyl)urea,
1-[4-(5-cyano-6-chloro-2-pyridyloxy)-3,5-dichlorophenyl]-3-(2,6-difluorobenzoyl)urea,
1-[4-(5-cyano-6-chloro-2-pyridyloxy)-3,5-dimethylphenyl]-3-(2-chlorobenzoyl)urea,
1-[4-(5-cyano-6-chloro-2-pyridyloxy)-3,5-dimethylphenyl]-3-(2,6-difluorobenzoyl)urea,
1-[4-(5-cyano-6-chloro-2-pyridyloxy)-3,5-dimethylphenyl]-3-(2,6-dichlorobenzoyl)urea,
1-[4-(5-cyano-6-chloro-2-pyridyloxy)-3,5-dimethylphenyl]-3-(2-chloro-6-fluorobenzoyl)urea,
1-[4-(5-cyano-6-chloro-2-pyridyloxy)-3,5-dimethylphenyl]-3-(4-chlorobenzoyl)thiourea,
1-[4-(5-cyano-6-chloro-2-pyridyloxy)-3,5-dimethylphenyl]-3-(2,6-fluorobenzoyl)urea,
1-[4-(3-chloro-5-methyl-2-pyridyloxy)-3,5-dichlorophenyl]-3-(2-chloro-6-fluorobenzoyl)urea.
1-[4-(3-chloro-5-methyl-2-pyridyloxy)-3,5-dichlorophenyl]-3(2-chlorobenzoyl)thiourea.
1-[4-(3-chloro-5-methyl-2-pyridyloxy)-3,5-dichlorophenyl]-3-benzoyl thiourea.
1-[4-(3-chloro-5-methyl-2-pyridyloxy)-3-methylphenyl]3-(2-chlorbenzoyl)urea.
1-[4-(3-chloro-5-methyl-2-pyridyloxy)-2,5-dimethylphenyl]-3-(2,6-difluorobenzoyl)urea.
1-[4-(3,5-dimethyl-2-pyridylthio)-3,5-dichlorophenyl]-3-((2,6-difluorobenzoyl)urea.
1-[4-(3,5-dimethyl-2-pyridylthio)-3,5-dichlorophenyl]-(3-chlorobenzoyl)thiourea.
1-[4-(3,5-dimethyl-2-pyridylsulfonyl)-3,5-dichlorophenyl]-3-(2,6-difluorobenzoyl)urea.
1-[4-(3-methyl-5-chloro-2-pyridylthio)-3,5-dichlorophenyl]-3-(2,6-difluorobenzoyl)urea.
1-[4-(3-methyl-5-chloro-2-pyridylthio)-3,5-dichlorophenyl]-3-(2-chlorobenzoyl)thiourea.
1-[4-(3-methyl-5-chloro-2-pyridylsulfonyl)-3,5-dichlorophenyl]-3-(2,6-difluorobenzoyl)urea.
1-[4-(3-methyl-5-chloro-2-pyridylthio)-3-methylphenyl]-3-(2-chlorobenzoyl)urea.
1-[4-(3-methyl-5-chloro-2-pyridylsulfonyl)-3-methylphenyl]-3-(2,6-difluorobenzoyl)urea.
1-[4-(3-methyl-5-bromo-2-pyridylthio)-3,5-dichlorophenyl]-3-(2-chlorobenzoyl)urea.
1-[4-(3,6-dimethyl-2-pyridylthio)-3,5-dichlorophenyl-3-(2,6-difluorobenzoyl)urea.
1-[4,6-dimethyl-2-pyridyloxy)-2,5-dimethylphenyl]-3-(2,6-difluorobenzoyl)urea.
1-[4-(3-chloro-5-methyl-2-pyridyloxy)-2-methyl-5-chlorophenyl]-3-(2-chlorobenzoyl)urea.
1-[4-(3-chloro-5-methyl-2-pyridyloxy)-2-methyl-5-chlorophenyl]-3-(2-chlorobenzoyl)thiourea.

The novel benzoyl ureas of this invention can be conveniently prepared by one or more methods. For example, the compounds of this invention may be prepared by reacting a substituted aniline 3 with a benzoylisocyanate 2 according to Scheme I.

SCHEME I

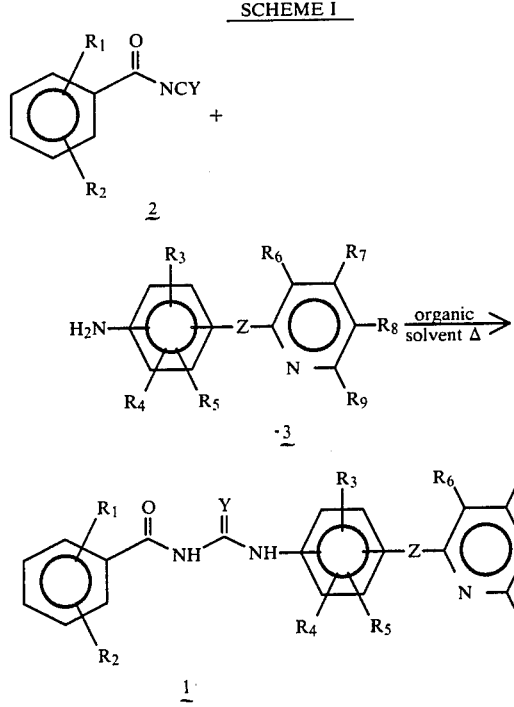

Wherein, $R_1$, $R_2$, $R_3$, $R_4$, $R_5$, $R_6$, $R_7$, $R_8$, $R_9$, Y and Z have the meaning given in Formula 1.

Alternatively, the novel compounds may be prepared by the reaction of a pyridyloxyphenylisocyanate 5 with a benzamide 4 according to Scheme II.

SCHEME II

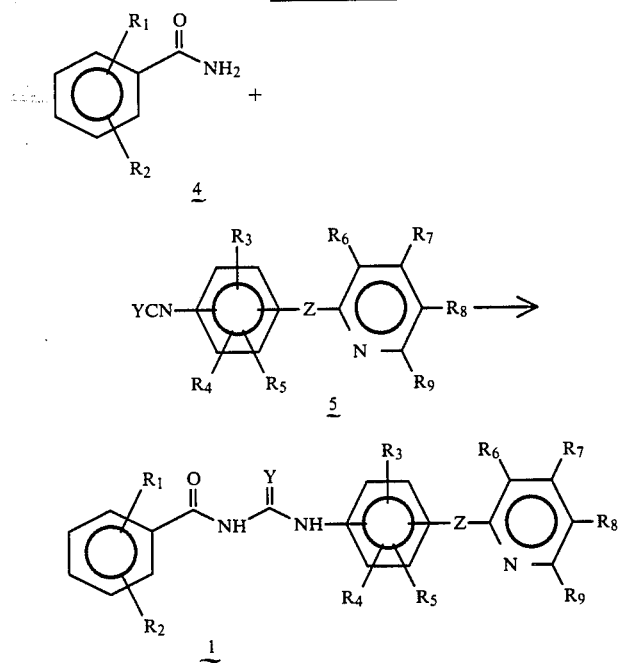

Wherein: $R_1$, $R_2$, $R_3$, $R_4$, $R_5$, $R_6$, $R_7$, $R_8$, $R_9$, Y and Z have the meaning given in Formula 1.

The novel compounds can also be prepared by the reaction of a substituted urea or thiourea 6 with benzoylchloride 7 according to Scheme III

Scheme III

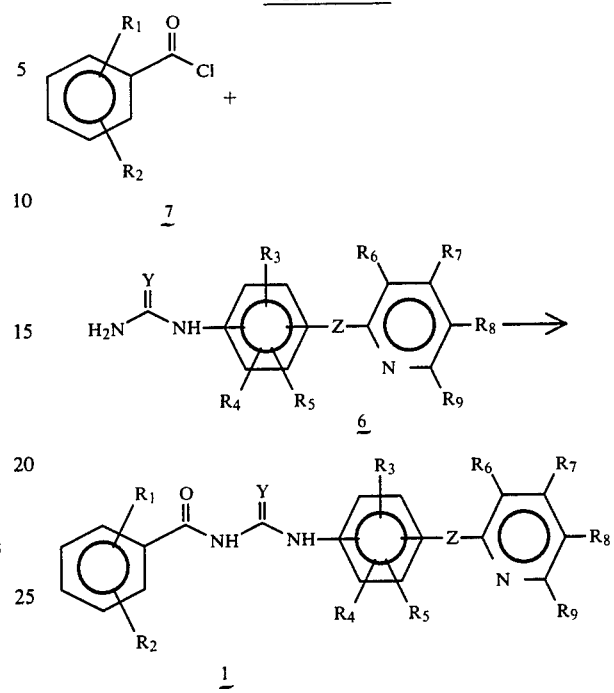

wherein the substituents are as previously indicated.

In general, the reactions illustrated in Scheme I, II and III can be carried out in organic solvents like aromatic hydrocarbon and the like, halogenated hydrocarbon. Solvents like toluene and 1,2-dichloroethane are preferred. These reactions proceed at temperatures ranging from room temperature to 150° C.

The intermediates shown in Scheme I, II and III can be prepared according to generally accepted procedures. Thus, the substituted benzoylisocyanate 2 can be prepared from the corresponding benzamide following the general procedure of Speziale et. al., *J. Org. Chem.* 27, 3742 (1962).

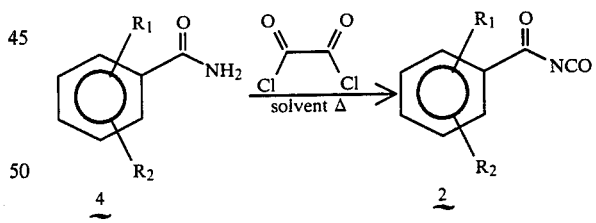

The substituted benzoylisothiocyanate can be prepared in high yield by the reaction of benzoyl chloride with potassium thiocyanate. Aromatic hydrocarbon or chlorinated hydrocarbon can be used as solvent. This procedure, in general, is similar to that of Ambelang, et. al., *J. Am. Chem. Soc.* 61, 632 (1937)

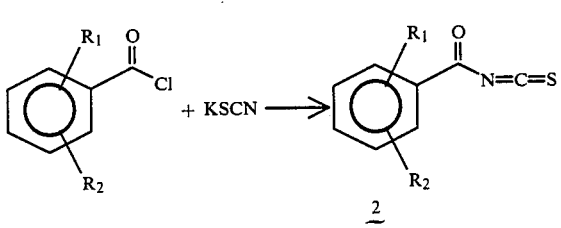

The aniline 3 can be prepared according to either Scheme IV, V or VI shown below.

SCHEME IV

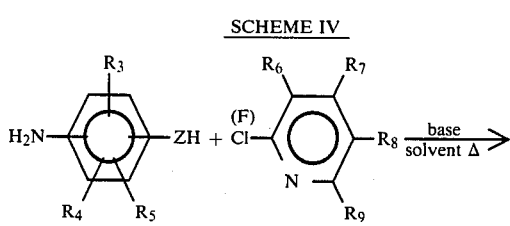

9       8

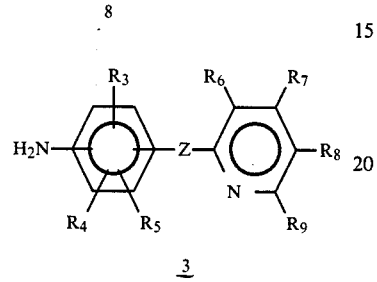

3

SCHEME V

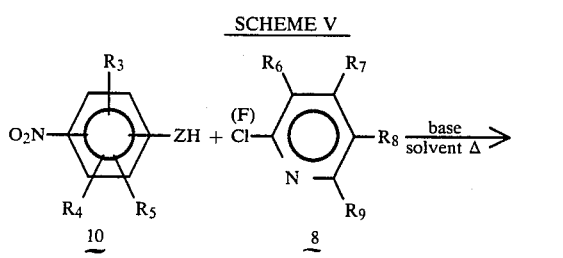

10      8

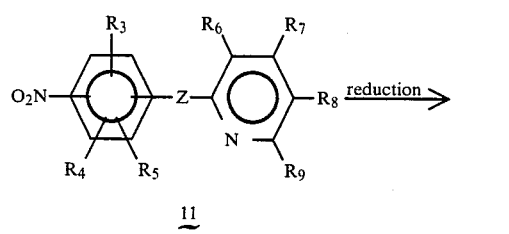

11

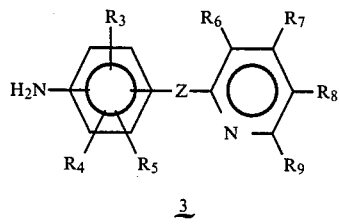

3

SCHEME VI

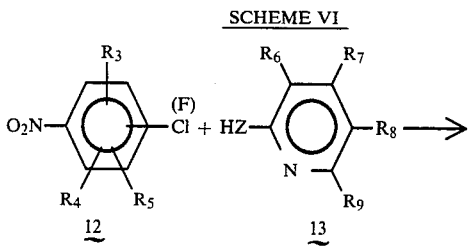

12      13

-continued
SCHEME VI

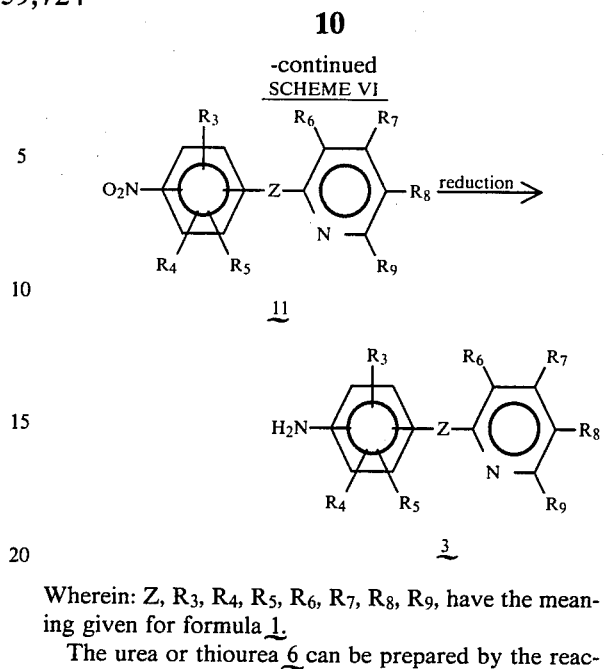

11

3

Wherein: Z, $R_3$, $R_4$, $R_5$, $R_6$, $R_7$, $R_8$, $R_9$, have the meaning given for formula 1.

The urea or thiourea 6 can be prepared by the reaction of aniline 3 with phosgene or thiophosgene followed by ammonium hydroxide.

The reaction of aminophenol or aminothiophenol 9 with substituted 2-chloropyridine 8 proceeds in the presence of base in inert solvent at elevated temperature to give the substituted aniline 3. The bases suitable for this reaction are potassium carbonate, sodium hydride, potassium hydroxide and sodium hydroxide. Suitable solvents are toluene, acetone, dimethylformamide, and dimethylsulfoxide.

The reaction of nitrophenol or nitrothiophenol 10 with substituted 2-chloropyridine 8 proceeds in the similar manner as in the reaction described above.

The reduction of nitroether (or nitrothioether) 11 to the aniline 3 can be achieved under hydrogen atmosphere using a heterogeneous hydrogenation catalyst. Suitable catalyst includes platinum or palladium on carbon or Raney nickel/iron. The pressure ranging from 50~120 PSI at ambient temperature can be applied. Suitable solvents includes aromatic hydrocarbon or alcohol.

The reduction of nitroether 11 can also be achieved by chemical methods using the procedure of E. Enders, et. al., GB No. 1,456,964.

The intermediates such as nitrophenol, nitrothiophenol, chloronitrobenzene, aminophenol, aminothiophenol or substituted 2-chloropyridine are available commercially or may be prepared by well known methods from chemical literature.

The aniline 3 can be converted to the isocyanate or isothiocyanate 5 by the reaction with phosgene or thiophosgene as shown below.

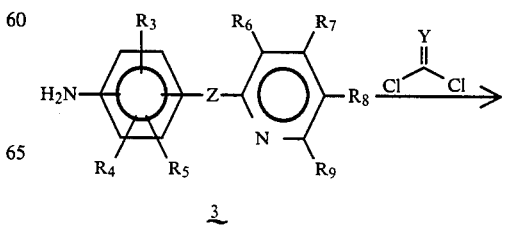

3

-continued

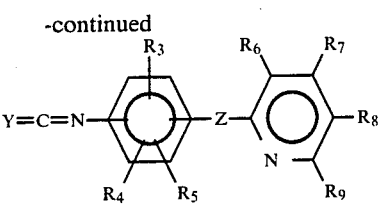

wherein Y, Z, $R_3$, $R_4$, $R_5$, $R_6$, $R_7$, $R_8$, and $R_9$, have the meaning previously given.

The compounds contemplated in this invention may be applied as insecticides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, dimethylformanide or nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein prevent attack by insects and mites upon plants or other material to which the pesticides are applied, and they have relatively high residual toxicity. With respect to plants, they have a high margin of safety in that when used in sufficient amount to kill or repel the insects, they do not burn or injure the plant, and they resist weathering which includes wash-off caused by rain, decomposition by ultraviolet light, oxidation, or hydrolysis in the presence of moisture or, at least, such decomposition, oxidation, and hydrolysis as would materially decrease the desirable pesticidal characteristic of the toxicants or impart undesirable characteristics, for instance, phytotoxicity, to the toxicants. The toxicants are so chemically inert that they are now compatible with substantially any other constituents of the spray schedule, and they may be used in the soil, upon the seeds, or the roots of plants without injuring either the seeds or roots of plants.

Mixtures of the active compounds may be employed if desired as well as combinations of the active compounds of this invention with other biologically active compounds or synergists.

The following examples illustrate the best mode presently contemplated for the practice of the invention:

EXAMPLE 1

Part A: Preparation of 4-(3-methyl-5-cyano-2-pyridinoxy)-3,5-dichloroaniline.

To a 100 mL round bottom flask equipped with a water condenser, thermometer, magnetic stirrer, and under nitrogen atmosphere was added 2-chloro-3-methyl-5-cyanopyridine (7.10 g, 46.6 mmol), potassium carbonate (9.02 g, 65.2 mmol), 2,6-dichloro-4-aminophenol (10.77 g, 60.5 mmol), and dimethylformanide (70 mL). The resulting mixture was stirred at room temperature for 1 hour, 90° for 2 hours, and 110° for 3 hours. It was then cooled, filtered, and concentrated to give a brown mixture. This mixture was dissolved in 500 mL of toluene and washed with four 150 mL portions of 4% sodium hydroxide, water, and brine. It was then dried ($Na_2SO_4$) and concentrated to give the desired product as a brown solid (8.00 g, 27.2 mmol). m.p. 211.5°–212.5°.

Anal: $C_{13}H_9Cl_2N_3O$; Calcd: C, 53.08; H, 3.08; N, 14.29; Found C, 53.65; H, 3.06; N, 14.59.

The following compounds were also prepared in the manner set forth above:

4-(3-cyano-2-pyridoxy)-3,5-dichloroaniline—203° decomposed.

4-(5-cyano-2-pyridoxy)-3,5-dichloroaniline—m.p. 189°–190°

4-(3-chloro-5-cyano-2-pyridoxy)-3,5-dichloroaniline—m.p. 214°–217°

4-(3-methyl-5-nitro-2-pyridinoxy)-3,5-dichloroaniline—m.p. 167.5°–169.0°

Part B: Preparation of 1-[4-(3-methyl-5-cyano-2-pyridyloxy)-3,5-dichlorophenyl]-3-(2,6-dichlorobenzoyl)urea.

To a 100 mL flask equipped with magnetic stirrer, condenser, under nitrogen atmosphere was added 4-(3-methyl-5-cyano-2-pyridinoxy)-3,5-dichloroaniline (1.7 g, 5.78 mmol) and toluene (15 mL). The resulting mixture was heated up to 90° to form a solution. A solution of 2,6-dichlorobenzoylisocyanate (2.0 g, 9.25 mmol) in 2 mL of toluene was added to the above solution. The resulting mixture was heated at 90° for 1.5 hours and then cooled. The cold reaction mixture was filtered and the solid was washed with cold toluene. The solid was vacuum dried to afford an orange solid (2.1 g, 4.11 mmol). m.p. 245°–246°

Anal: $C_{21}H_{12}Cl_4N_4O_3$; Calcd: C, 49.34; H, 2.37; N, 10.94; Found: C, 49.65; H, 2.27; N, 10.96.

EXAMPLES 1–32

In a manner similar to that employed in the preceding examples, and using one of the synthesis schemes previously disclosed, other urea compounds were prepared. The identity of the substituents on the generic formula and the analytical data are set forth in table I below:

TABLE I

Pyridyloxyaryl Benzoyl Ureas

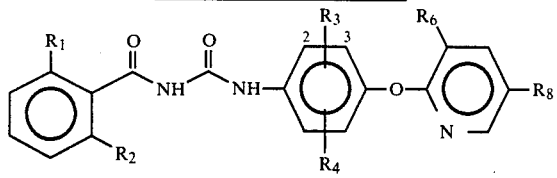

| Example | Molecular Formula | $R_1$ | $R_2$ | $R_3$ | $R_4$ | (1) | $R_6$ | $R_8$ | Calculated C | Calculated H | Calculated N | Found C | Found H | Found N |
|---|---|---|---|---|---|---|---|---|---|---|---|---|---|---|
| 1 | $C_{20}H_{10}Cl_2F_2N_4O_3$ | F | F | 3-Cl | 5-Cl | | CN | H | 51.86 | 2.18 | 12.09 | 51.98 | 2.30 | 11.89 |
| 2 | $C_{20}H_{10}Cl_3FN_4O_3$ | Cl | F | 3-Cl | 5-Cl | | CN | H | 50.08 | 2.10 | 11.68 | 50.35 | 2.26 | 11.58 |
| 3 | $C_{20}H_{10}Cl_4N_4O_3$ | Cl | Cl | 3-Cl | 5-Cl | | CN | H | 48.42 | 2.03 | 11.29 | 48.59 | 2.45 | 11.20 |
| 4 | $C_{20}H_{11}Cl_3N_4O_3$ | Cl | H | 3-Cl | 5-Cl | | CN | H | 52.03 | 2.40 | 12.14 | 52.28 | 2.67 | 12.09 |
| 5 | $C_{20}H_{10}Cl_3FN_4O_3$ | Cl | F | 3-Cl | 5-Cl | | H | CN | 50.08 | 2.10 | 11.68 | 52.84 | 2.45 | 11.67 |
| 6 | $C_{20}H_{10}Cl_2F_2N_4O_3$ | F | F | 3-Cl | 5-Cl | | H | CN | 51.86 | 2.18 | 12.09 | 51.94 | 2.05 | 12.09 |
| 7 | $C_{20}H_{11}Cl_3N_4O_3$ | Cl | H | 3-Cl | 5-Cl | | H | CN | 52.03 | 2.40 | 12.14 | 52.20 | 2.49 | 12.07 |
| 8 | $C_{21}H_{12}Cl_2F_2N_4O_3$ | F | F | 3-Cl | 5-Cl | | $CH_3$ | CN | 52.74 | 2.53 | 11.71 | 52.82 | 2.41 | 11.71 |
| 9 | $C_{21}H_{12}Cl_3F_1N_4O_3$ | Cl | F | 3-Cl | 5-Cl | | $CH_3$ | CN | 50.98 | 2.46 | 11.33 | 51.08 | 2.34 | 11.37 |
| 10 | $C_{21}H_{12}Cl_4N_4O_3$ | Cl | Cl | 3-Cl | 5-Cl | | $CH_3$ | CN | 49.34 | 2.37 | 10.94 | 49.65 | 2.27 | 10.96 |
| 11 | $C_{21}H_{13}Cl_3N_4O_3$ | Cl | H | 3-Cl | 5-Cl | | $CN_3$ | CN | 53.02 | 2.75 | 11.78 | 53.14 | 2.80 | 11.61 |
| 12 | $C_{20}H_9Cl_3F_2N_4O_3$ | F | F | 3-Cl | 5-Cl | | Cl | CN | 48.26 | 1.82 | 11.26 | 48.48 | 1.74 | 11.11 |
| 13 | $C_{20}H_{10}Cl_4N_4O_3$ | Cl | H | 3-Cl | 5-Cl | | Cl | CN | 48.41 | 2.03 | 11.29 | 49.25 | 2.09 | 10.89 |
| 14 | $C_{20}H_9Cl_4F_1N_4O_3$ | Cl | F | 3-Cl | 5-Cl | | Cl | CN | 46.72 | 1.76 | 10.90 | 46.88 | 1.67 | 10.79 |
| 15 | $C_{20}H_{12}Cl_2F_2N_4O_5$ | F | F | 3-Cl | 5-Cl | | $CH_3$ | $NO_2$ | 48.31 | 2.43 | 11.27 | 48.66 | 2.43 | 11.22 |
| 16 | $C_{20}H_{12}Cl_3F_1N_4O_5$ | Cl | F | 3-Cl | 5-Cl | | $CH_3$ | $NO_2$ | 46.76 | 2.35 | 10.91 | 46.88 | 2.41 | 10.86 |
| 17 | $C_{20}H_{13}Cl_3N_4O_5$ | Cl | H | 3-Cl | 5-Cl | | $CH_3$ | $NO_2$ | 48.46 | 2.64 | 11.30 | 48.76 | 2.72 | 11.23 |
| 18 | $C_{20}H_{12}ClFN_4O_3$ | Cl | F | H | H | M | H | CN | 58.48 | 2.94 | 13.64 | 58.53 | 2.90 | 13.66 |
| 19 | $C_{20}H_{13}Cl_2N_4O_3$ | Cl | H | H | H | M | H | CN | 61.16 | 3.34 | 14.26 | 61.27 | 3.31 | 14.23 |
| 20 | $C_{20}H_{12}ClN_4O_3$ | Cl | Cl | H | H | M | H | CN | 56.22 | 2.83 | 13.11 | 56.23 | 2.68 | 12.89 |
| 21 | $C_{22}H_{16}CLFN_4O_3$ | Cl | F | 2-$CH_3$ | 5-$CH_3$ | P | H | CN | 60.21 | 3.68 | 12.77 | 60.85 | 4.11 | 12.47 |
| 22 | $C_{22}H_{16}Cl_2N_4O_3$ | Cl | Cl | 2-$CH_3$ | 5-$CH_3$ | P | H | CN | 58.04 | 3.54 | 12.30 | 57.33 | 3.55 | 12.15 |
| 23 | $C_{22}H_{17}ClN_4O_3$ | Cl | H | 2-$CH_3$ | 5-$CH_3$ | P | H | CN | 62.91 | 4.08 | 13.34 | 64.32 | 4.30 | 13.16 |
| 24 | $C_{20}H_{12}F_2N_4O_3$ | F | F | H | H | M | H | CN | 60.97 | 3.07 | 14.22 | 61.32 | 3.15 | 14.05 |
| 25 | $C_{22}H_{16}F_2N_4O_3$ | F | F | 2-$CH_3$ | 5-$CH_3$ | P | H | CN | 62.76 | 3.83 | 13.31 | 63.03 | 3.94 | 13.07 |
| 26 | $C_{20}H_{11}Br_2ClN_4O_3$ | Cl | H | 3-Br | 5-Br | P | H | CN | 43.60 | 2.01 | 10.17 | 43.82 | 2.17 | 10.26 |
| 27 | $C_{20}H_{10}Br_2F_2N_4O_3$ | F | F | 3-Br | 5-Br | P | H | CN | 43.48 | 1.82 | 10.14 | 43.50 | 1.81 | 10.03 |
| 28 | $C_{20}H_{10}Br_2CLFN_4O_3$ | Cl | F | 3-Br | 5-Br | P | H | CN | 42.22 | 1.77 | 9.85 | 42.44 | 1.75 | 9.78 |
| 29 | $C_{20}H_{11}BrCl_2N_4O_3$ | Cl | H | 3-Cl | 5-Br | P | H | CN | 47.46 | 2.19 | 11.07 | 47.66 | 2.34 | 10.97 |
| 30 | $C_{20}H_{10}BrCl_3N_4O_3$ | Cl | Cl | 3-Cl | 5-Br | P | H | CN | 44.44 | 1.86 | 10.36 | 44.89 | 2.07 | 10.18 |
| 31 | $C_{20}H_{10}BrCl_2FN_4O_3$ | Cl | F | 3-Cl | 5-Br | P | H | CN | 45.84 | 1.92 | 10.69 | 45.87 | 2.02 | 10.65 |
| 32 | $C_{20}H_{10}BrClF_2N_4O_3$ | F | F | 3-Cl | 5-Br | P | H | CN | 47.32 | 1.98 | 11.04 | 47.25 | 2.05 | 11.02 |
| 33 | $C_{20}H_{11}Br_2ClN_4O_2S$ | Cl | H | 3-Br | 5-Br | P | H | CN | 42.39 | 1.06 | 9.89 | 43.66 | 2.07 | 9.86 |

(1) Attachment of pyridyloxy groups to phenyl group Meta (M) or para (P)

Certain representative examples of the new compounds were evaluated to determine their pesticidal activity against mites and certain insects, including a caterpillar and a beetle. The new compounds were also tested for phytotoxicity on important economic crops including bean, soybean, corn, tomato and cotton. The new compounds were further evaluated for mammalian toxicity.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The test concentrations in parts per million by weight employed in the tests described hereinbelow were obtained by appropriate dilutions of the stock suspension with water. Certain of the test compounds were also prepared by dissolving 375 mg of compound in 7.5 ml of dimethylformamide. Fifteen ml of acetone containing 37.5 mg (10 percent of the weight of test compound) of an alkylphenoxy polyethoxyethanol surfactant, as a wetting/emulsifying/dispersing agent was added to the dimethylformamide solution. Fifty-two and a half ml of water was mixed into the dimethylformamide-acetone mixture to give roughly 75 ml of a suspension containing the compound in solution or in finely divided form. The thus prepared stock suspension contained 0.5 percent by weight of compound. The test procedures were as follows:

Southern Armyworm Leaf Spray Bait Test

Larvae of the southern armyworm (Spodoptera eridania, (Cram.)), reared on Tendergreen bean plants at a temperature of 80°±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 40 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for up to five days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (*Epilachna varivestic*, Muls.), reared on Tendergreen bean plants at a temperature of 80°±5° F. and 50±5 percent relative humidity, were the test insects. For certain of the tests second instar larvae (weighing about 6 mg) of the Mexican bean beetle (*Epilachna varivestis*, Muls.), reared on Seiva Pole lima bean plants at a temperature of 80°±5° F. and 50±5 percent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 40 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F., for five days. Although the larvae could easily consume the leaf within 24 to 48 hours, no more food was added. Larvae which were unable to move the length of the body, even upon stimulation, were considered dead.

The biological properties of certain representative examples of the compounds of this invention are set forth in Table II below.

TABLE II

Biological Properties of Representative Benzoyl Ureas

| Example | Activity 500 ppm SAW[1] | MBB[2] |
|---|---|---|
| 2 | A | A |
| 3 | A | A |
| 4 | A | A |
| 5 | A | A |
| 6 | A | A |
| 7 | A | A |
| 8 | A | A |
| 9 | A | A |
| 10 | A | A |
| 11 | A | A |
| 12 | A | A |
| 13 | A | A |
| 14 | A | A |
| 15 | A | A |
| 16 | A | A |
| 17 | A | A |
| 18 | A | A |
| 21 | A | A |
| 22 | A | A |
| 23 | A | C |
| 24 | A | C |
| 25 | A | A |
| 26 | A | A |
| 27 | A | A |

TABLE II-continued

Biological Properties of Representative Benzoyl Ureas

| Example | Activity 500 ppm SAW[1] | MBB[2] |
|---|---|---|
| 28 | A | A |
| 29 | A | A |
| 30 | A | A |
| 31 | A | A |
| 32 | A | A |
| 33 | A | A |

[1] Southern Armyworm
[2] Mexican Bean Beetle
[3] Code = A = Complete control
B = Moderate control
C = No control

EXAMPLES 33–37

In order to demonstrate the enhanced biological activity against the Southern Armyworm, representative benzoyl ureas were compared with known products. The results are set forth in Table III below:

TABLE III

Comparison Of Representative Benzoyl Ureas With Known Compounds Against Southern Armyworm

| Compound | Application rate (ppm) | Percent Control after 5 days |
|---|---|---|
| 1-(4-chlorophenyl)-3-(2,6-difluorobenzoyl)urea[1] | 10 | 100 |
|  | 5 | 40 |
| 1-[4-(4-cyanophenoxy)-3-chlorophenyl]-3-(2,6-difluorobenzoyl)urea[2] | 31 | 70 |
|  | 15 | 75 |
|  | 7.5 | 36 |
| 1-[4-(3-chloro-5-cyano-2-pyridyloxy)-3,5-dichlorophenyl]-3-(2-chlorobenzoyl) urea | 31 | 100 |
|  | 8 | 100 |
|  | 2 | 100 |
| 1-[4-(3-methyl-5-cyano-2-pyridyloxy)-3,5-dichlorophenyl]-3-(2-chloro-6-fluorobenzoyl) urea | 4 | 100 |
|  | 2 | 87 |
| 1-[4-(5-cyano-2-pyridyoxy)-3,5-dichlorophenyl]-3-(2-chlorobenzoyl)urea | 31 | 100 |
|  | 8 | 100 |
|  | 2 | 90 |

[1] Dimilin, a known compound.
[2] related known compound. (U.S. Pat. No. 4,194,005)

EXAMPLES 38–41

In order to demonstrate the enhanced biological activity against Heliothis spp., representative benzoyl ureas were compared with known products. The results are set forth in Table IV below:

TABLE IV

Comparison Of Representative Benzoyl Ureas With Known Compounds Against Heliothis

| Compound | LD$_{50}$ (ppm) H. Zea | H. Virescens |
|---|---|---|
| 1-(4-chlorophenyl)-3-(2,6-difluorobenzoyl)urea[1] | 500 | 31 |
| 1-[4-(5-cyano-2-pyridyloxy)-3,5-dichlorophenyl]-3-(2-chloro-benzoyl)urea | 3 | 4 |
| 1-[4-(5-cyano-2-pyridyloxy)-3,5-dichlorophenyl]-3-(2,6-difluorobenzoyl)urea | 4 | 3 |

[1] Dimilin, a known compound

Although the invention has been illustrated by the foregoing examples, it is not to be construed as being limited to the materials employed therein; but rather, the invention encompasses the generic area as hereinafter disclosed. Various modifications and embodiments can be made without departing from the spirit and scope thereof.

What is claimed is:

1. A compound of the formula:

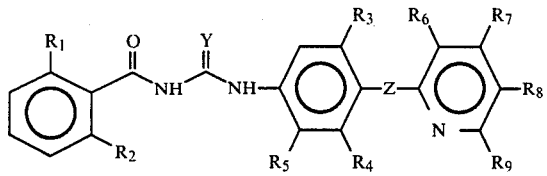

wherein:
Y represents oxygen;
Z represents oxygen;
$R_1$ and $R_2$ are independently hydrogen, halogen or lower alkyl;
$R_3$ and $R_4$ are independently halogen or methyl;
$R_5$ represents hydrogen, halogen or methyl;
$R_6$ represents hydrogen or lower alkyl;
$R_7$ represents hydrogen;
$R_8$ represents cyano; and
$R_9$ represents hydrogen.

2. The compound of claim 1 wherein $R_1$ and $R_2$ are independently hydrogen or halogen, $R_3$ and $R_4$ are independently halogen, $R_5$ is hydrogen and $R_6$ is hydrogen or methyl.

3. The compound of claim 1 wherein $R_1$ and $R_2$ are independently halogen, $R_3$ and $R_4$ are independently halogen, $R_5$ is hydrogen and $R_6$ is hydrogen.

4. The compound of claim 1 wherein $R_1$ and $R_2$ are independently halogen, $R_3$ and $R_4$ are independently halogen, $R_5$ is hydrogen and $R_6$ is methyl.

5. The compound of claim 1 wherein $R_1$ is halogen, $R_2$ is hydrogen, $R_3$ and $R_4$ are independently halogen, $R_5$ is hydrogen and $R_6$ is hydrogen.

6. The compound of claim 1 wherein $R_1$ is halogen, $R_2$ is hydrogen, $R_3$ and $R_4$ are independently halogen, $R_5$ is hydrogen and $R_6$ is methyl.

7. The compound of claim 1 which is 1-[4-(5-cyano-2-pyridyloxy)-3,5-dichlorophenyl]-3-(2-chloro-6-fluorobenzoyl)urea.

8. The compound of claim 1 which is 1-[4-(5-cyano-2-pyridyloxy)-3,5-dichlorophenyl]-3-(2,6-difluorobenzoyl)urea.

9. The compound of claim 1 which is 1-[4-(5-cyano-2-pyridyloxy)-3,5-dichlorophenyl]-3-(2-chlorobenzoyl)urea.

10. The compound of claim 1 which is 1-[4-(3-methyl-5-cyano-2-pyridyloxy)-3,5-dichlorophenyl]-3-(2,6-difluorobenzoyl)urea.

11. The compound of claim 1 which is 1-[4-(5-cyano-2-pyridyloxy)-3,5-dibromophenyl]-3-(2-chloro-6-fluorobenzoyl)urea.

12. The compound of claim 1 which is 1-[4-(5-cyano-2-pyridyloxy)-3-chloro-5-bromophenyl]-3-(2,6-difluorobenzoyl)urea.

13. A pesticide composition comprising an acceptable carrier and a pesticidally effective amount of the compound of claim 1.

14. A pesticide composition comprising an acceptable carrier and a pesticidally effective amount of the compound of claim 2.

15. A pesticide composition comprising an acceptable carrier and a pesticidally effective amount of the compound of claim 3.

16. A pesticide composition comprising an acceptable carrier and a pesticidally effective amount of the compound of claim 4.

17. A pesticide composition comprising an acceptable carrier and a pesticidally effective amount of the compound of claim 5.

18. A pesticide composition comprising an acceptable carrier and a pesticidally effective amount of the compound of claim 9.

19. A pesticide composition comprising an acceptable carrier and a pesticidally effective amount of the compound of claim 6.

20. A method of controlling insects and acarids which comprises subjecting said pests to a pesticidally effective amount of a compound of claim 1.

21. A method of controlling insects and acarids which comprises subjecting said pests to a pesticidally effective amount of a compound of claim 2.

22. A method of controlling insects and acarids which comprises subjecting said pests to a pesticidally effective amount of a compound of claim 3.

23. A method of controlling insects and acarids which comprises subjecting said pests to a pesticidally effective amount of a compound of claim 4.

24. A method of controlling insects and acarids which comprises subjecting said pests to a pesticidally effective amount of a compound of claim 5.

25. A method of controlling insects and acarids which comprises subjecting said pests to a pesticidally effective amount of the compound of claim 9.

26. A method of controlling insects and acarids which comprises subjecting said pests to a pesticidally effective amount of the compound of claim 6.

* * * * *